(12) United States Patent
Kalikow

(10) Patent No.: US 6,277,131 B1
(45) Date of Patent: Aug. 21, 2001

(54) LADDER-TYPE MEDICAL CLIP FEEDING MECHANISM

(75) Inventor: Irving Kalikow, Swampscott, MA (US)

(73) Assignee: Microline, Inc, Beverly, MA (US)

( * ) Notice: Subject to any disclaimer, the term of this patent is extended or adjusted under 35 U.S.C. 154(b) by 0 days.

(21) Appl. No.: 09/504,572

(22) Filed: Feb. 15, 2000

(51) Int. Cl.$^7$ .................................................. A61B 17/04
(52) U.S. Cl. ............................................. 606/143; 227/19
(58) Field of Search ..................................... 606/142, 143

(56) References Cited

U.S. PATENT DOCUMENTS

| | | | |
|---|---|---|---|
| Re. 36,720 | * | 5/2000 | Green et al. .......................... 606/151 |
| 3,638,847 | * | 2/1972 | Noiles .................................... 606/143 |
| 4,522,207 | * | 6/1985 | Klieman et al. ...................... 606/143 |
| 4,674,504 | * | 6/1987 | Klieman et al. ...................... 606/143 |
| 5,246,450 | * | 9/1993 | Thornton et al. ..................... 606/143 |
| 5,626,585 | * | 5/1997 | Mittelstadt et al. .................. 606/143 |
| 5,772,673 | * | 6/1998 | Cuny et al. ........................... 606/142 |
| 6,059,799 | * | 5/2000 | Aranyi et al. ........................ 606/143 |

* cited by examiner

Primary Examiner—Gary Jackson
(74) Attorney, Agent, or Firm—Don Halgren

(57) ABSTRACT

The present invention relates to a clip feeder arrangement for supportive receipt in a handle of a medical clip stapling gun to permit the advancement of a plurality of clips seriatim by a trigger mechanism in the handle to a location between a pair of pincher jaws. A distalmost clip of that plurality of clips is being advanced to the jaws prior to advancement of the remaining plurality of clips. The feeder arrangement comprises a ladder arranged within a U-shaped cartridge having a proximal end and a distal end. The distalmost clip is moved distally away from the ladder by a clip feeder bar mechanism which is arranged for first advancing the distalmost clip in the cartridge to a location between the jaws. The remaining plurality of clips are then also advanced distally by the ladder, both of the advancement motions occurring in a single distal advance of the clip feeder bar mechanism.

16 Claims, 4 Drawing Sheets

LADDER-TYPE MEDICAL CLIP FEEDING MECHANISM

BACKGROUND OF THE INVENTION

1. Field of the Invention

This invention relates to feeding arrangements for medical clip and stapling devices, particularly for the pinching or clipping of blood vessels or for the closure of wounds, and is related to commonly owned, co-pending U.S. application Ser. No.: 09/504,498, filed Feb. 15, 2000, entitled "Medical Clip Device with Cyclical Pusher Mechanism", and incorporated herein by reference in its entirety.

2. Prior Art

Surgical staplers and clips have been used more and more to replace suturing and for closing wounds or to tie-off blood vessels during a surgical procedure or other traumatic medical event. Such surgical clips and stapler applicators generally comprise of closed jaws, which crimp a U-shaped clip flat across the tissues to be tied or sutured. Typically, such an application device is arranged through the spaced clips in a sequential manner, those clips being fed serially to the jaws.

The tools typically in use dispense such clips to the jaws sequentially, the distalmost clip being pinched, and the next adjacent clip immediately therebehind being advanced immediately adjacent the pinched clip. Examples of such clip feeding arrangements are shown in U.S. Pat. No. 5,246,450 to Thornton et al, showing a clip feeding and dispenser mechanism which uses a spring to force the movement of clips in line with an applicator.

The U.S. Pat. No. 3,638,847 to Noiles et al., shows a ratchet driven cartridge for advancing sequentially a plurality of staples. U.S. Pat. No. 5,626,585 to Mittelsteate et al., shows a ligating clip-advancing device for advancing a plurality of clips along a track between a pair of pinched jaws. The U.S. Pat. No. 4,674,504 to Klieman et al., shows a spring activated homeostatic clip applicator wherein a double ratchet apparatus advances clips through a magazine to cause a clip-feed blade to slide through the magazine to place a clip in the deforming jaws. Each of the above identified prior art patents is incorporated herein by reference in their entirety.

It is an object of the present invention, to provide a medical clip feeding mechanism which is an improvement over the prior art.

It is a further object of the present invention, to provide a medical clip feeding mechanism which advances the distalmost clip into the jaws of the stapling device prior to the advancement of the next available clip moving along the feed track.

It is yet a still further object of the present invention, to provide a simple and easy to use clipper feeder arrangement which is tolerant of a slight dimensional irregularity in the clips or staples utilized by the stapling device or gun.

BRIEF SUMMARY OF THE INVENTION

The present invention relates to a clip or staple feeding arrangement for providing clips or staples to the biased-open jaws of a stapling gun. The new staple clip gun comprises a handle at one end thereof, for holding and actuating the clip stapling arrangement. The handle comprises a housing and a trigger mechanism for actuating the jaws and clip feeding mechanism. The housing has an opening through which a proximal end of a barrel is supported. The barrel has a distal end where the jaws, utilized for feeding and pinching the clips or staples, is located. A generally U-shaped frame member is arranged through the length of the inside of the barrel. The frame member has a plurality of bridges spaced along its elongated length. A jaw control rod, moveable proximally and distally, is arranged on the bridges, to provide the pinching movement to the jaws at the distal end of the barrel. The frame has several portions along its length on its lowermost side, having elongated slots therein. The distalmost slot is arranged near the distal end of the barrel, and a mid-slot is arranged along a mid portion of the frame's length. A ramp-like projection is arranged at a location on each side of the distalmost slot and mid-portion slot in the frame, which ramps act as cam tracks to guide pins extending from the sides of upstanding fingers of an elongated, spring stainless steel clip feeder bar into engagement with the distalmost clip and the elongated, slotted ladder respectively. The elongated, slotted ladder pushes all but the distalmost clip distally along in the frame.

The barrel is arranged to receive a clip cartridge at its rearmost opening at the housing in the handle. The frame is arranged to receive the clip or staple cartridge which cartridge includes the elongated, slotted ladder. The clips are generally U-shaped, and have leg members which extend distally from the housing. The clips and the elongated ladder are arranged to be slidable within the generally U-shaped channel, the channel providing their enclosure in the package. The elongated ladder has a plurality of elongated slots or holes of generally rectangular shape arranged longitudinally down the middle portion thereof. The ladder has a distal end, which abuts the last (proximalmost) clip within the cartridge.

In each of the preferred embodiments of the present invention, about twenty U-shaped clips or staples may be held seriatim in the cartridge. Each clip being in an abutting and in a pushing arrangement with its adjacent distal clip.

The elongated cycling clip feeder bar is arranged within the barrel and supported beneath the frame member therewithin. The cycling clip feeder has a distalmost finger of ramp-like configuration, having a pin extending from each transverse side thereof. The clip feeder also has a proximal finger extending upwardly in a spaced relation to the elongated slot location in the lowermost side of the mid portion location of the frame member. The elongated cycling clip feeder is advanceable distally and returnably proximally in a cyclic manner according to the actuation of the trigger mechanism within the handle of the clip device. The proximate finger has a pin extending transversely from each side thereof in a manner similar to that of the distalmost finger.

Squeezing of the trigger mechanism in the handle cycles the longitudinal distal advancement of the elongated clip feeder relative to the frame member. Release of that trigger advances simultaneously the proximal fingers with the distal finger, the proximal finger is permitted by the spring action of the clip feeder, and the ramp-like tracks on the side of the slot in the frame, to enter the hole of the elongated ladder corresponding to the location of the opening in the lower portion of mid portion of the frame. The same longitudinal advance of the clip feeder effects simultaneous advancement of the distal finger. As the distalmost finger advances, its spring like bias pushes it into the slot in the frame where permitted by the ramp-like tracks. The distal finger then touches the backside of the distalmost clip, to push it distally and effect its entry between the pincher jaws. The trigger mechanism effects the squeezing together of the open pincher jaws by distally advancing a crimp box on the push rod to crimp the clip or staple onto a body component to be pinched close.

Release of the trigger mechanism also opens the jaws and advances the proximal finger on the clip feeder member, which finger has traveled the length of the rectangular slot or hole in the ladder at its location adjacent its opening in the framed member. As the proximal finger enters the distal end of that rectangular hole in the ladder, it continues to move within that rectangular hole until it comes to the distal end of that hole, where it then begins to push the ladder distally a spaced distance, to then also push upon the series of clips within the cartridge, thus effecting delivery of the next available clip to its stand-by position at the distal end of the frame. Squeezing of the trigger mechanism effects the rearward or proximate cycle of movement of the clip feeder bar proximally, and the side pins of each respective finger engaging the ramp walls of the lower side of the slot on the the frame member, so as to also bias downwardly the fingers out of the way of the respective clips and ladder openings or holes thereadjacent. A generally oval path is thus generated by the fingers, the upper side of the oval path comprising the fingers engaging the ladder and the distalmost clip respectively, and the lower side of the oval path being traveled by the fingers and their clip feeder member returning to their proximalmost position to await re-activation by the trigger in the handle. The clip feeder bar is thus returned to its proximalmost location.

When the trigger is in the "relaxed" position (after one actuation), the jaws are open and the cinch box is in is proximalmost location. The distalmost finger has pushed a clip between the jaws and the proximal finger has pushed the ladder "one stop" distally, pushing all the clips including the distalmost clip to the end of the cartridge. When the trigger is squeezed, the push rod is advanced to advance the cinch box, to close the jaws. Both fingers are cammed downwardly by virtue of the side pins engaging the ramps adjacent the slot in the frame, so as to move out of the way from hitting the next distalmost clip and out of the way of the ladder as the fingers are pulled proximally. When the trigger is released, the cinch box is caused to retract, permitting the jaws to bias themselves open, and then the clip feeder bar pushes a new distal clip into the jaws, and then the proximal finger pushes the ladder and the whole series of clips distally.

The invention thus comprises a clip feeder arrangement for supportive receipt in a handle of a medical clip stapling gun to permit the advancement of a plurality of clips seriatim in said clip feeder arrangement by a trigger mechanism in said handle, to feed said clips to a location between a pair of pincher jaws. A distalmost clip of the plurality of clips is advanced to the jaws prior to advancement of the remaining plurality of clips. The feeder arrangement comprises a U-shaped cartridge having a proximal end and a distal end, the cartridge containing the plurality of clips, a frame for supporting the cartridge, an elongated ladder member arranged in the cartridge to push the clips distally upon activation of a pusher mechanism by the trigger mechanism. The ladder member has a plurality of elongated openings therein to permit distal advancement of the distalmost clip prior to the distal advancement of the remainder of the clips in the cartridge. The pusher mechanism includes a clip feeder bar cyclically engagable with the ladder, the clip feeder bar actuated by the trigger mechanism in the handle for distal and proximal movement. The elongated ladder has a distal end for pushing the clips in the cartridge. The clip feeder bar has a distal finger and a proximal finger thereon, wherein the distal finger pushes the distalmost clip to a location between the pair of jaws, and the proximal finger pushes the ladder to push the remaining clips in the cartridge after the distalmost clip is disposed between the jaws. The fingers are arranged to permit their cammed displacement from engagement with the clips and the ladder during its return to its starting position below the frame. The frame has a clip feeder guide plate therebeneath, to support the fingers during a portion of the movement of the fingers and the clip feeder bar. The fingers have a pair of pins extending transversely therefrom to cam the fingers into and out of engagement with the clips and the ladder by riding upon a ramp-like cam track adjacent the slot in the frame member. Release of the trigger mechanism actuates advancement of the distalmost clip into the jaws and then activates advancement of all of the clips in the cartridge. An elongated barrel encloses the mechanism, to enclose and protect the clip feeder mechanism therewithin. The barrel mates into an opening in the handle for communication of the trigger mechanism and the clip feeder mechanism. The clips may be of slight differing dimensions within the cartridge.

The invention also comprises a method of sequentially feeding a plurality of clips to a set of jaws in a medical clip stapling gun comprising the steps of placing a clip containing cartridge in a frame for feeding said clips to a pair of pincher jaws, disposing an elongated ladder in the cartridge so as to push the clips to a distal end of the cartridge, arranging a plurality of elongated openings in the ladder to permit an advancing pusher mechanism from pushing the ladder until the pusher mechanism first engages a distal end of an opening in the ladder, pushing a distalmost clip in the cartridge by a distal end of the pusher mechanism, and subsequently pushing the ladder by the pushing mechanism to push the remainder of the clips in said cartridge distally. The method includes the steps of pinching the distalmost clip between the jaws by actuation of a trigger mechanism in a handle portion of the stapling gun, and recycling the pusher mechanism proximally so as to permit the sequential advance of the next distalmost clip to a location between the jaws.

Thus what has been shown as a unique feeder mechanism for supplying a plurality of clips or staples in a sequential manner, wherein the distalmost clip is advanced into a pair of squeezeable jaws ahead of the next adjacent clip being fed forward into its stand-by location. In engagement by the proximalmost fingers into an elongated slot, permits a tolerance of dimensional inadequacy within a respective clips or staples within the series of staples maintained within the cartridge.

BRIEF SUMMARY OF THE DRAWINGS

The objects and advantages of the present invention will become more apparent, when viewed in conjunction with the following drawings, in which.

DESCRIPTION OF THE PREFERRED EMBODIMENTS

Figure 1:
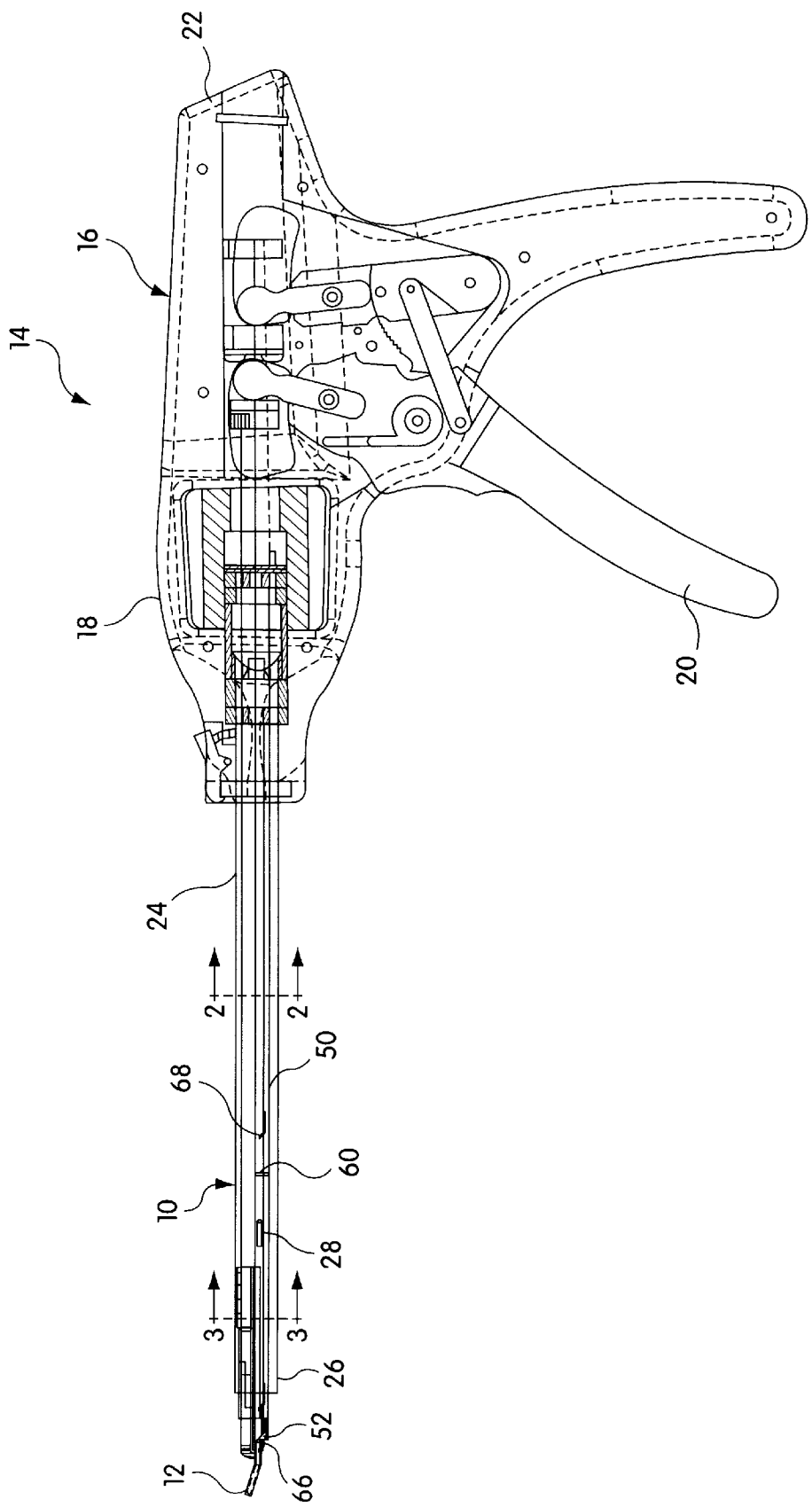
FIG. 1 is a side elevational view, partly in section, of a homeostatic clip delivery gun respective according to the principals of the present invention.
Figure 4:
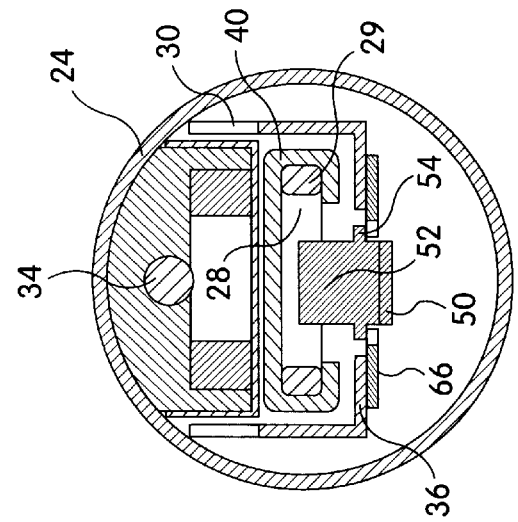
FIG. 4 is a view similar to FIG. 3, showing the feeder dyed finger in its engagement orientation.
Figure 3:
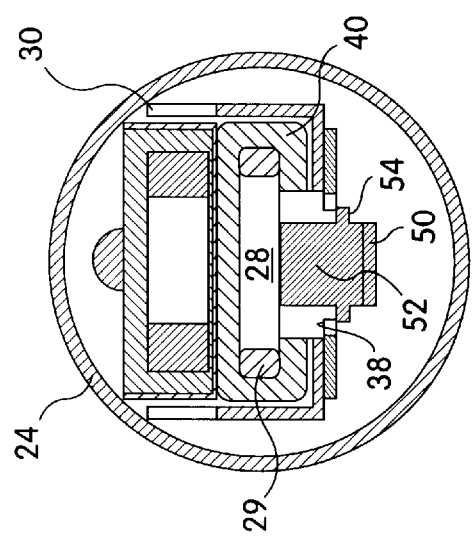
FIG. 3 is a cross section view taken along the lines 3—3 of FIG. 1.
Figure 2:
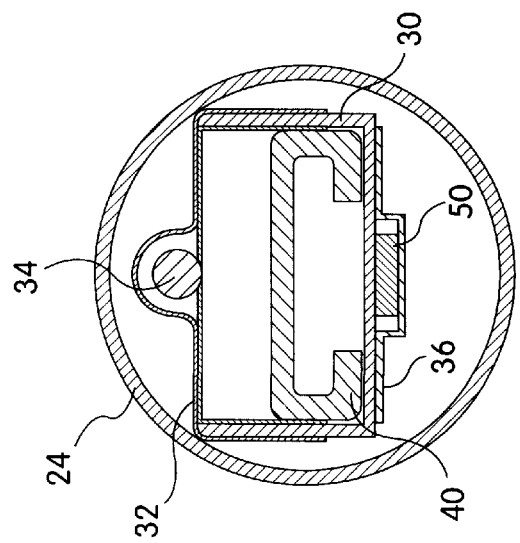
FIG. 2 is cross sectional view taken along the lines 2—2 of FIG. 1.
Figure 5:
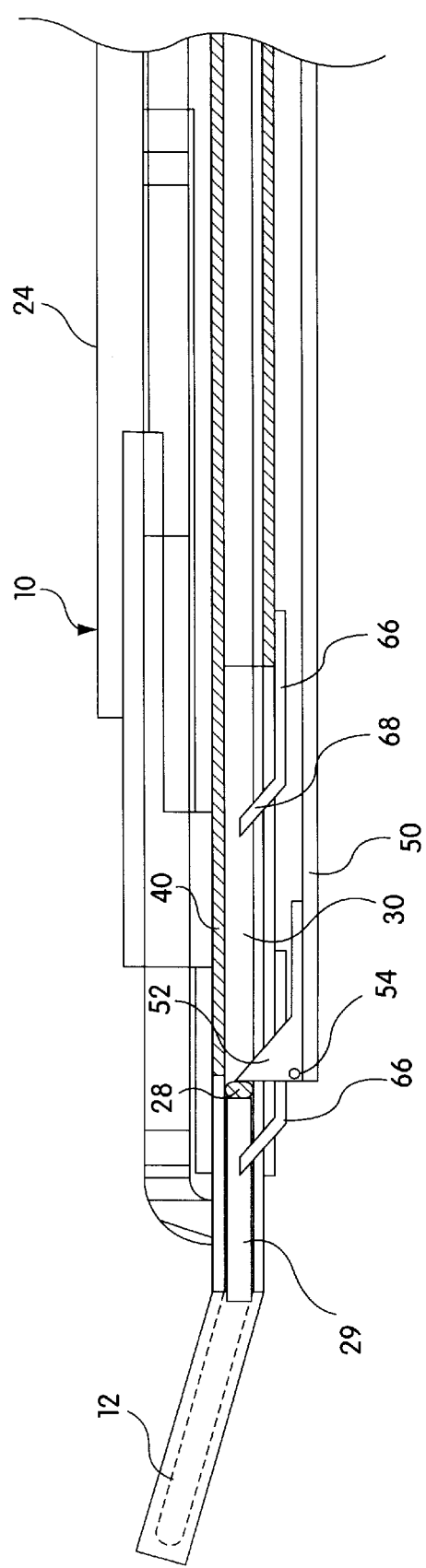
FIG. 5 is a sectional view of the distal most end of the feeder apparatus.

Referring now to the drawings in detail, and particularly to FIG. 1, there is shown the present invention which comprises a clip or staple advancing and feeding arrangement 10 for providing clips or staples to the jaws 12 of a stapling gun 14. The new staple clip gun 14 comprises a handle 16 at a first end thereof, for holding and actuating the clip stapling arrangement 10. The handle 16 comprises a housing 18 and a trigger mechanism 20 for actuating the jaws 12 and the clip feeding mechanism 10. The housing 18 has an opening 22 through which a proximal end of a barrel 24 is supported. The barrel 24 has a distal end 26 where the jaws 12, utilized for feeding and pinching the clips or staples 28, is located. A generally U-shaped frame member 30, shown more clearly in FIGS. 2, 3, 4 and 6, is arranged through the length of the inside of the barrel 24. The frame 30 has a plurality of bridges 32 spaced along its elongated length. A jaw control rod 34, moveable proximally and distally, is supportively arranged on the bridges 32, as may be seen in FIG. 2, to provide the pinching movement to the jaws 12 at the distal end 26 of the barrel 24. The frame 30 has several portions along its length on its lower-most side 36, having elongated slots 38 therein, as may be seen in FIGS. 3, 4 and 6. The distalmost slot 38' is arranged near the distal end 26 of the barrel 24, and a mid-slot 38" is arranged along a mid portion of the frame's length, as may be seen in FIG. 6.

The barrel 24 is arranged to receive a clip cartridge 40 at its rearmost opening 22 at the housing 18 in the handle 16. The frame 30 is arranged to receive the U-shaped (cross-section) clip or staple cartridge 40 which includes a plurality of clips or staples 28 and an elongated ladder 42, best seen in FIG. 6. The clips 28 are generally U-shaped, and have leg members 29 which extend distally away from the housing 18. The clips 28 and the elongated ladder 42 are arranged to be slidable within the generally U-shaped cartridge 40, which provides their enclosure in the package. The elongated ladder 42 has a plurality of elongated slots or holes 44 of generally rectangular shape arranged longitudinally down the middle portion thereof, as may be seen in FIG. 6. The ladder 42 has a distal end 48, which abuts the last (proximalmost) clip 28 within the cartridge 40.

Figure 6:
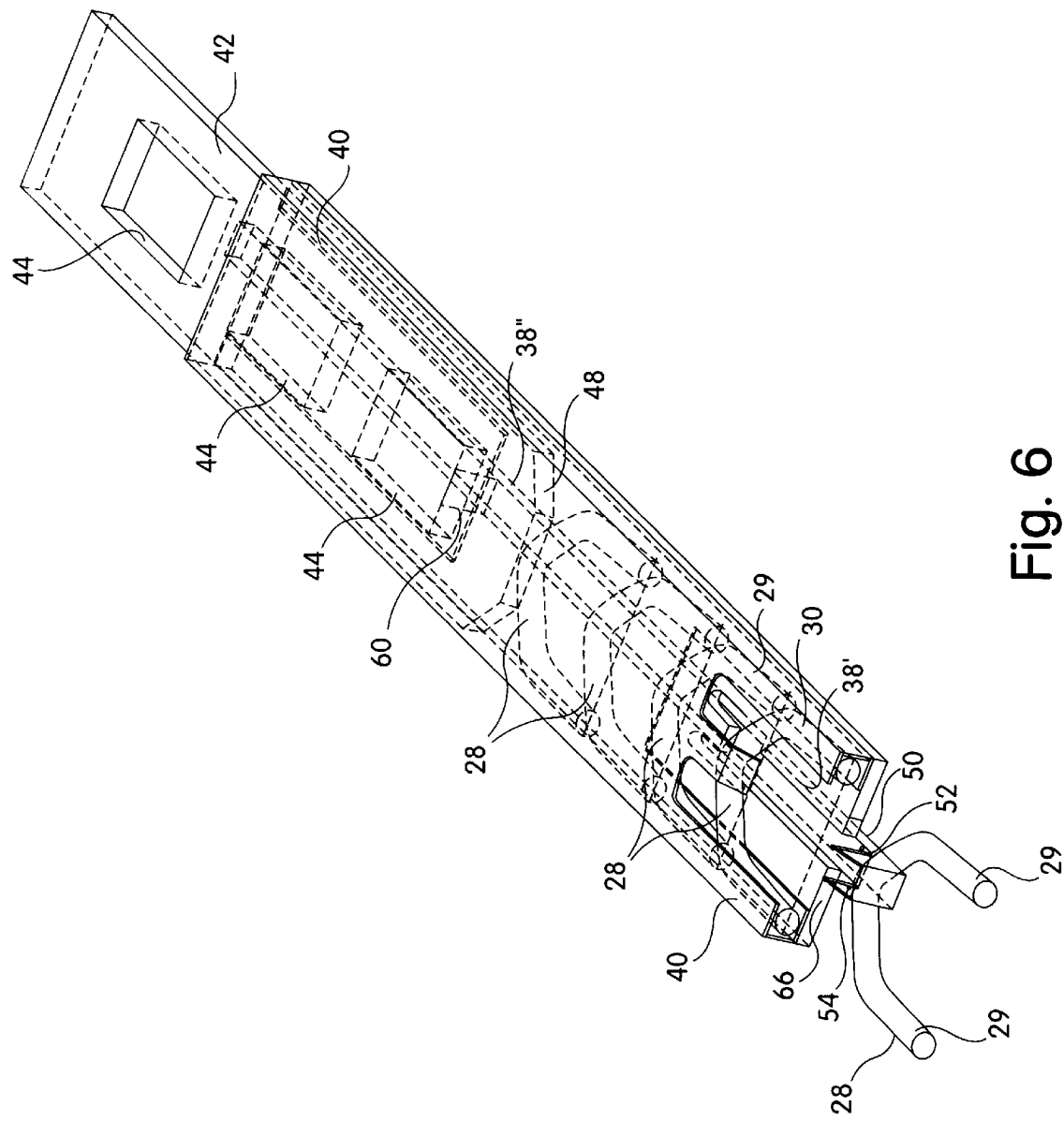
FIG. 6 is a view, in perspective of the feeder cartridge.

In each of the preferred embodiments of the present invention, about twenty U-shaped clips or staples 28 may be held seriatim in the cartridge 40. Each clip 28 is in an abutting and in a pushing arrangement with its adjacent distal clip 28, as shown in FIG. 6.

An elongated cycling clip feeder member or bar 50 is arranged within the barrel 24 and is supported beneath the frame member 30 therewithin. The clip feeder member or bar 50 has a distalmost finger 52 of ramp-like configuration, having a short pin 54 extending from each transverse side thereof, as may be seen in FIGS. 3, 4 and 6. The cycling clip feeder bar 50 also has a proximal finger 60 extending upwardly in a spaced relation to the elongated slot location in the lowermost side of the frame member 30, as may be seen in FIG. 6. The elongated clip feeder bar 50 is movable distally and proximally according to the actuation of the trigger mechanism 20 within the handle 16 of the clip device 14. The proximate finger 60 also has a pin (not shown for clarity), extending transversely from each side thereof in a manner similar to that of the distalmost finger 52. The pins 54 on the fingers 52 and 60 cam the fingers 52 and 60 out of engagement with the clips 28 through sliding engagement with the ramps 66 and 68 adjacent the slots 38 in the frame member 30, as the feeder bar 50 is drawn proximally.

The squeezing of the trigger mechanism 20 cycles the longitudinal distal advancement of the elongated clip feeder bar 50 relative to the frame member 30. Release of that trigger simultaneously advances the proximal finger with the distal finger 52, the proximal finger 60 is permitted by the upward spring action thereof, to enter one of the holes 44 of the elongated ladder 42 corresponding to the location of the slot opening 38" in the lower mid portion of the frame 30, as embodied in FIG. 1, and shown in FIG. 6. The same advance of the clip feeder bar 50 effects advancement of its distalmost finger 52. As the distalmost finger 52 advances, it engages the backside of the distalmost clip 28, as represented in FIG. 6, to push thereon and effect its entry between the pincher jaws, (not shown in FIG. 6, for clarity). The trigger mechanism 20 effects the squeezing together of the open pincher jaws 12 to crimp the clip or staple 28.

Release of the trigger mechanism 20 opens the jaws 12 and advances the proximal finger 60, which has by then traveled the length of the rectangular hole 44 in the ladder 42 at its location adjacent its opening 38" in the frame member 30. As the proximal finger 60 engages the distal end of that rectangular hole 44 in the ladder 42, it then begins to push the ladder 42 distally a spaced distance, to push upon the entire series of clips 28 within the cartridge 40 thus effecting delivery of the next available staple or clip 28 to its "stand-by" position at the distal end 26 of the barrel 24 after the former end or distalmost clip 28 has been pushed between the jaws 12 by the distalmost finger 52. Movement of the trigger mechanism 20 effects rearward or proximate cycle of movement of the clip feeder bar 50, and the side pins 54 of each respective finger 52 and 60 engaging the lower side of the ramps 66 and 68 adjacent the slot 38 on the lower side of the frame member 30, so as to bias the fingers 52 and 60 down and out of the way of the respective clips 28 and ladder openings or holes 44 respectively thereadjacent as the feeder bar 50 cycles rearwardly completing a generally "oval" path "C". The clip finger bar 50 is then returned to its proximalmost location with the pins 54 riding under the feeder guide plate 66, to await a further actuation of the trigger mechanism 20, which would recycle the entire clip cartridge 20 and feeder bar mechanisms 50 accordingly. Thus what has been shown as a unique feeder mechanism for supplying a plurality of clips or staples in a sequential manner, wherein the distalmost clip is advanced into a pair of squeezable jaws ahead of the next adjacent clip which is fed forward into its stand-by location. Engagement by the proximalmost finger into an elongated slot before the ladder is forced to move while the distalmost finger advances the distalmost clip and permits a tolerance of dimensional inadequacy with respective clips or staples within the series of staples maintained within the cartridge.

What is claimed is:

1. A clip feeder arrangement supportively received in a handle of a medical clip stapling gun to permit the advancement of a plurality of clips seriatim in said clip feeder arrangement by a trigger mechanism in said handle, to feed said clips to a location between a pair of pincher jaws, a distalmost clip of said plurality of clips being advanced to said jaws prior to advancement of the remaining plurality of clips, said feeder arrangement comprising:

a U-shaped cartridge having a proximal end and a distal end, said cartridge containing said plurality of clips;
a frame for supporting said cartridge;
an elongated ladder member arranged in said cartridge to push said clips distally upon activation of a clip feeder bar mechanism by said trigger mechanism, said ladder member having a plurality of elongated openings therein to permit distal advancement of the distalmost clip prior to distal advancement of the remainder of said clips in said cartridge.

2. The clip feeder mechanism as recited in claim 1, wherein said clip feeder bar is cyclically engagable with said ladder, said clip feeder bar being actuated by said trigger mechanism in said handle for distal and proximal movement.

3. The clip feeder mechanism as recited in claim 1, wherein said elongated ladder has a distal end for pushing said clips in said cartridge.

4. The clip feeder mechanism as recited in claim 2, wherein said clip feeder bar has a distal finger and a proximal finger thereon, wherein said distal finger pushes said distalmost clip to a location between said pair of jaws, and said proximal finger pushes said ladder to push said remaining clips in said cartridge after said distalmost clip is disposed between said jaws.

5. The clip feeder mechanism as recited in claim 4, wherein said fingers are arranged to permit their cammed displacement from engagement with said clips and said ladder during its return to its starting position below said frame.

6. The clip feeder mechanism as recited in claim 4, wherein said frame has a clip feeder guide plate therebeneath, to support said fingers during a portion of said movement of said fingers and said clip feeder bar.

7. The clip feeder mechanism as recited in claim 4, wherein said fingers have a pair of pins extending transversely therefrom to cam said fingers into and out of engagement with said clips and said ladder by riding upon a cam track adjacent said slot in said frame member.

8. The clip feeder mechanism as recited in claim 4, wherein actuation of said trigger mechanism commonly actuates advancement of said distalmost clip into said jaws and advancement of said clips in said cartridge.

9. The clip feeder mechanism as recited in claim 4, wherein an elongated barrel encloses said mechanism, to enclose and protect said clip feeder mechanism therewithin.

10. The clip feeder mechanism as recited in claim 8, wherein said barrel mates into an opening in said handle for communication of said trigger mechanism and said clip feeder mechanism.

11. The clip feeder mechanism as recited in claim 8, wherein said clips may be of differing dimensions within said cartridge.

12. A method of sequentially feeding a plurality of clips to a set of jaws in a medical clip stapling gun comprising the steps of:

placing a clip containing cartridge in a frame for feeding said clips to a pair of pincher jaws;

disposing an elongated ladder in said cartridge so as to push said clips to a distal end of said cartridge;

arranging a plurality of elongated openings in said ladder to permit an advancing clip feeder bar mechanism from pushing said ladder until said clip feeder bar mechanism first engages a distal end of an opening in said ladder;

pushing a distalmost clip in said cartridge by a distal end of said clip feeder bar mechanism; and subsequently pushing said ladder by said clip feeder bar mechanism to push the remainder of said clips in said cartridge distally.

13. The method of sequentially feeding a plurality of clips to a set of jaws in a medical clip stapling gun as recited in claim 12, including the steps of:

pinching said distalmost clip between said jaws by actuation of a trigger mechanism in a handle portion of said stapling gun.

14. The method of sequentially feeding a plurality of clips to a set of jaws in a medical clip stapling gun as recited in claim 13, comprising the steps of:

recycling said clip feeder bar mechanism proximally so as to permit the sequential advance of the next distalmost clip to a location between said jaws.

15. The method of sequentially feeding a plurality of clips to a set of jaws in a medical clip stapling gun comprising the steps of:

pushing an elongated slotted ladder in a frame of said gun by a clip feeder bar in said frame, to push a plurality of clips distally in one motion of said clip feeder bar; and pushing a distalmost clip of said plurality of clips into a set of pincher jaws of said gun before the remainder of said plurality of clips are moved distally by said one motion of said clip feeder bar.

16. The method of sequentially feeding a plurality of clips to a set of jaws in a medical clip stapling gun, as recited in claim 15, including the step of:

engaging said distalmost clip by said clip feeder bar before said slotted ladder and said plurality of clips is advanced distally by said pusher bar in said one motion of said clip feeder bar.

* * * * *